United States Patent
Van Der Zouw

(10) Patent No.: US 10,215,954 B2
(45) Date of Patent: Feb. 26, 2019

(54) FOCUS MONITORING ARRANGEMENT AND INSPECTION APPARATUS INCLUDING SUCH AN ARRANGEMENT

(71) Applicant: ASML Netherlands B.V., Veldhoven (NL)

(72) Inventor: Gerbrand Van Der Zouw, Waalre (NL)

(73) Assignee: ASML Netherlands B.V., Veldhoven (NL)

(*) Notice: Subject to any disclaimer, the term of this patent is extended or adjusted under 35 U.S.C. 154(b) by 0 days.

(21) Appl. No.: 15/379,918

(22) Filed: Dec. 15, 2016

(65) Prior Publication Data

US 2017/0176714 A1 Jun. 22, 2017

(30) Foreign Application Priority Data

Dec. 18, 2015 (EP) .................................... 15201344

(51) Int. Cl.
*G02B 7/28* (2006.01)
*G01N 21/47* (2006.01)
(Continued)

(52) U.S. Cl.
CPC .......... *G02B 7/285* (2013.01); *G01N 21/4795* (2013.01); *G02B 7/32* (2013.01); *G02B 21/247* (2013.01); *G03F 9/7026* (2013.01)

(58) Field of Classification Search
CPC ...... G01N 21/4795; G02B 7/285; G02B 7/32; G02B 21/247; G03F 9/7026
See application file for complete search history.

(56) References Cited

U.S. PATENT DOCUMENTS

| 4,695,158 A | * | 9/1987 | Kotaka | ................... G02B 7/36 250/201.3 |
| 5,001,333 A | * | 3/1991 | Marshall | ........... G11B 7/08582 250/201.5 |

(Continued)

FOREIGN PATENT DOCUMENTS

| JP | S57-125910 A | 8/1982 |
| JP | 2001-242375 A | 9/2001 |

(Continued)

OTHER PUBLICATIONS

Wang et al., "Dual-confocal Auto-focus Sensing System in Ultrafast Laser Application," IEEE Sensors Conference, Nov. 2010; pp. 486-489.

(Continued)

*Primary Examiner* — Sang H Nguyen
(74) *Attorney, Agent, or Firm* — Sterne, Kessler, Goldstein & Fox P.L.L.C.

(57) ABSTRACT

A focus monitoring arrangement (1000) is provided for a scatterometer or other optical system. A first focus sensor (510) provides a first focus signal (S1-S2) indicating focus relative to a first reference distance (z1). A second focus sensor (1510) for providing a second focus signal (C1-C2) indicating focus relative to a second reference distance (z2). A processor (1530) calculates a third focus signal by combining the first focus signal and the second focus signal. By varying the proportions of the first and second focus signals in calculating the third focus signal, an effective focus offset can be varied electronically, without moving elements.

15 Claims, 8 Drawing Sheets

(51) Int. Cl.
*G02B 7/32* (2006.01)
*G02B 21/24* (2006.01)
*G03F 9/00* (2006.01)

(56) References Cited

U.S. PATENT DOCUMENTS

| | | | | |
|---|---|---|---|---|
| 5,345,072 A * | 9/1994 | Hayashi | ............... | G11B 7/0912 250/201.5 |
| 5,502,708 A * | 3/1996 | Morimoto | ............. | G11B 7/005 369/109.01 |
| 5,537,382 A * | 7/1996 | McLaughlin | .... | G11B 20/10009 341/59 |
| 5,557,597 A * | 9/1996 | Lee | ...................... | G11B 7/0912 250/201.5 |
| 5,774,432 A * | 6/1998 | Alon | ..................... | G11B 7/0909 369/112.26 |
| 5,905,919 A * | 5/1999 | Ide | ......................... | G02B 7/346 396/104 |
| 6,222,996 B1 * | 4/2001 | Nonaka | .................... | G02B 7/32 396/104 |
| 6,636,699 B2 * | 10/2003 | Owada | .................... | G02B 7/36 396/104 |
| 2002/0056802 A1 * | 5/2002 | Hiroyuki | ................ | G11B 7/131 250/201.5 |
| 2006/0033921 A1 | 2/2006 | Den Boef et al. | | |
| 2006/0066855 A1 | 3/2006 | Boef et al. | | |
| 2006/0261243 A1 * | 11/2006 | Park | ..................... | G11B 7/0945 250/201.5 |
| 2007/0237056 A1 * | 10/2007 | Hineno | ................ | G11B 7/1353 369/112.05 |
| 2008/0151228 A1 | 6/2008 | Hugers | | |
| 2009/0152440 A1 * | 6/2009 | Altendorf | .......... | G01B 11/0608 250/201.4 |
| 2010/0201963 A1 | 8/2010 | Cramer et al. | | |
| 2010/0328655 A1 | 12/2010 | Den Boef | | |
| 2011/0027704 A1 | 2/2011 | Cramer et al. | | |
| 2011/0043791 A1 | 2/2011 | Smilde et al. | | |
| 2011/0069292 A1 | 3/2011 | Den Boef | | |
| 2011/0261339 A1 | 10/2011 | Van Boxmeer et al. | | |
| 2012/0044470 A1 | 2/2012 | Smilde et al. | | |
| 2012/0123581 A1 | 5/2012 | Smilde et al. | | |
| 2012/0236696 A1 * | 9/2012 | Usui | .................... | G11B 7/08511 369/44.23 |
| 2013/0070334 A1 | 3/2013 | Kim et al. | | |
| 2013/0135978 A1 * | 5/2013 | Ide | ........................ | G11B 7/0917 369/53.28 |
| 2013/0250162 A1 * | 9/2013 | Sasaki | ...................... | G02B 7/30 348/345 |
| 2013/0258310 A1 | 10/2013 | Smilde et al. | | |
| 2013/0271740 A1 | 10/2013 | Quintanilha | | |
| 2014/0071330 A1 * | 3/2014 | Zhang | ................... | H04N 5/2258 348/345 |
| 2014/0139814 A1 | 5/2014 | Cramer et al. | | |
| 2014/0233040 A1 | 8/2014 | Gergen et al. | | |
| 2014/0269244 A1 * | 9/2014 | Yamasaki | ............ | G02B 5/1876 369/112.05 |
| 2014/0293019 A1 * | 10/2014 | Jang | ...................... | H04N 13/004 348/51 |
| 2015/0341543 A1 * | 11/2015 | Yokozeki | ............ | H04N 5/23229 348/353 |
| 2015/0358542 A1 * | 12/2015 | Sato | ........................ | H04N 5/265 348/239 |
| 2016/0134802 A1 * | 5/2016 | Inoue | ................... | H04N 5/23212 348/349 |
| 2016/0165126 A1 * | 6/2016 | Mishima | ............ | H04N 5/23212 382/255 |

FOREIGN PATENT DOCUMENTS

| | | |
|---|---|---|
| WO | WO 2012/126718 A1 | 9/2012 |
| WO | WO 2013/178422 A1 | 12/2013 |
| WO | WO 2014/082938 A1 | 6/2014 |
| WO | WO 2016/050453 A1 | 4/2016 |

OTHER PUBLICATIONS

International Search Report and Written Opinion of the International Searching Authority directed to related International Patent Application No. PCT/EP2016/079856, dated Feb. 28, 2017; 14 pages.

* cited by examiner

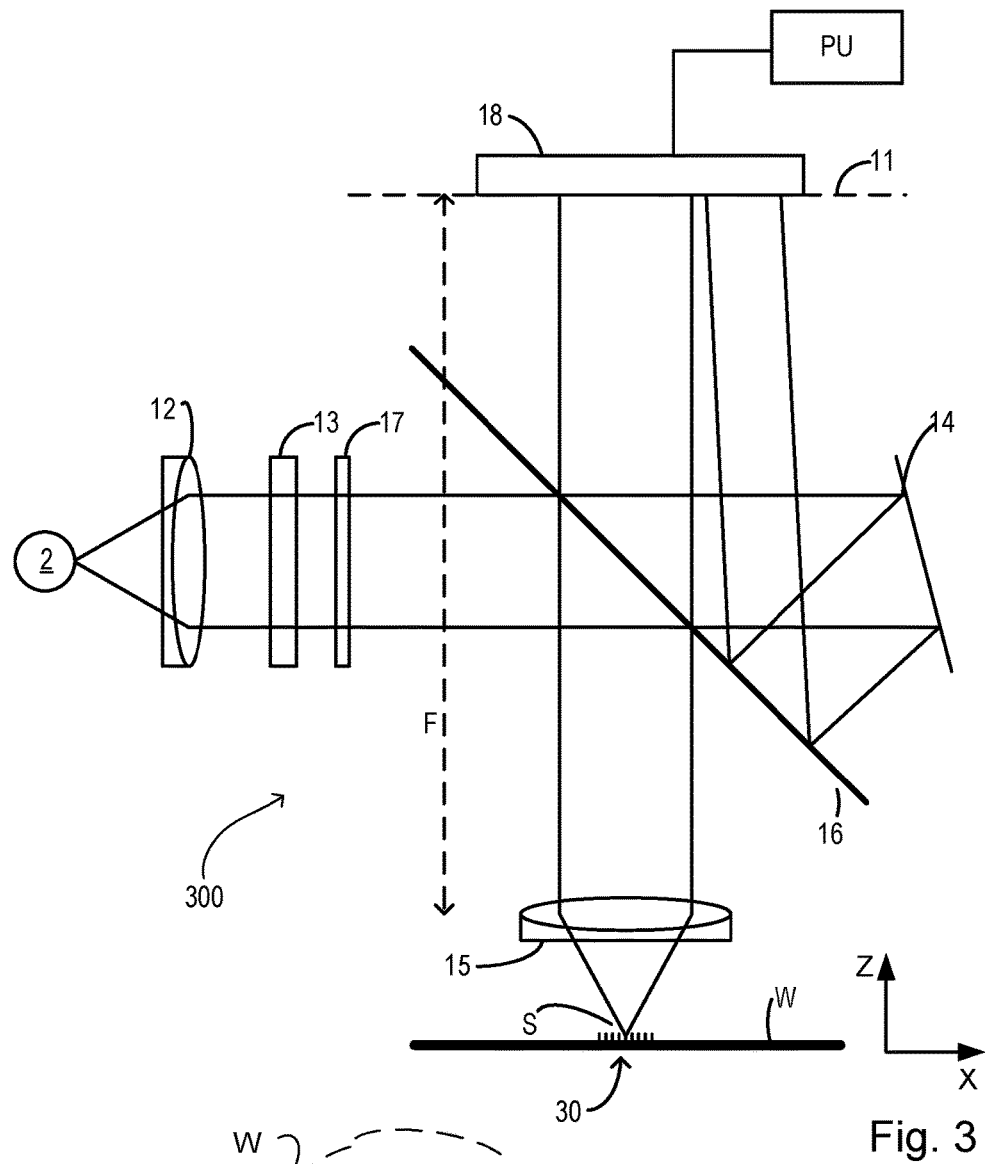
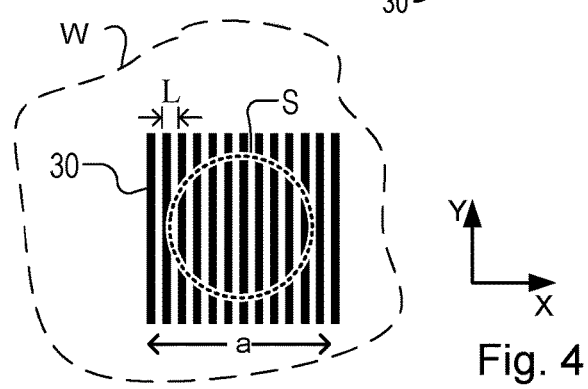
Fig. 3
Fig. 4

FOCUS MONITORING ARRANGEMENT AND INSPECTION APPARATUS INCLUDING SUCH AN ARRANGEMENT

FIELD

The present invention relates to focus monitoring arrangements for optical systems. The invention may be applied or example in inspection apparatus and lithographic apparatuses usable, for example, in the manufacture of devices by lithographic techniques.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 2012126718. Methods and scatterometers are also disclosed in US20110027704A1, US2006033921A1 and US2010201963A1. In addition to scatterometry to determine parameters of a structure made in one patterning step, the methods and apparatus can be applied to perform diffraction-based overlay measurements. Diffraction-based overlay metrology using dark-field image detection of the diffraction orders enables overlay measurements on smaller targets. Examples of dark-field imaging metrology can be found in international patent applications US2010328655 A1 and US2011069292 A1. Further developments of the technique have been described in published patent applications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference. The invention is not limited in application to any particular type of inspection apparatus, or even to inspection apparatuses generally.

A common problem in inspection apparatuses and other optical systems is one of controlling focusing of the optical system onto a target. Whether the optical system is for inspection by imaging, by scatterometry or for other purposes such as treatment of surfaces, many systems require real-time control of focus of the optical system, within very tight tolerances. A focus control arrangement for a scatterometer of the type described above is disclosed for example in published patent application US20080151228A. Light reflected from the target is imaged with deliberate focus error on two photodetectors. Comparing the illuminated area between the two photodetectors allows an indication of defocus to be obtained, and the direction of defocus to be identified. The contents of that application are incorporated herein by reference.

Current instruments using the known arrangement can achieve focus accuracy within around ±200 nanometers. However, the known arrangement also suffers from limitations in use. The focusing light to share the optical system with other radiations that relate to the main function of the optical system. These other radiations may be referred to as the working radiation to distinguish them from the focus control radiation. A single wavelength with limited power is generally used for focusing. However the working radiation being used by the instrument for exposure or inspection may be different, and focusing properties of the optical system at these different wavelengths may be different as a result. Known inspection apparatuses have mechanisms to apply an offset in the focus control arrangement, so that it can be used to focus the optical system for different wavelengths of working radiation.

One method of applying such an offset in the known focus control arrangement is to introduce an adjustable physical offset. This has the advantage of accurately shifting the focus by a known amount, but requires mechanical moving parts and causes delays when switching between different working radiation wavelengths. Accordingly, in some current apparatuses an electronic offset is introduced. This electronic offset can be switched instantaneously, but does not give an accurately known focus shift and reduces dynamic range of the focus control arrangement. There is therefore a desire for an improved electronic method of adjusting a focus control arrangement.

In a pending international patent application PCT/EP2015/070410, not published at the present priority date, a focus control arrangement with improved dynamic range and noise rejection can be obtained by applying an interferometric technique and lock-in detection in a focus control arrangement. Use of lock-in detection also allows different wavelengths of radiation to be used for focus monitoring, allowing good quality control over a wider range of targets. The techniques of the pending patent application can be employed in addition to the techniques disclosed below, if desired. The contents of the pending patent application are hereby incorporated by reference.

SUMMARY

The invention in a first aspect provides a focus monitoring arrangement for an optical system, comprising:

a first focus sensor for providing a first focus signal indicating focus relative to a first reference distance;

a second focus sensor for providing a second focus signal indicating focus relative to a second reference distance, the second reference distance being offset from the first reference distance;

a processor for calculating a third focus signal that indicates distance relative to a third reference distance, the third focus signal being calculated by combining the first focus signal and the second focus signal.

By varying the proportions of the first focus signal and the second focus signal, the processor can effectively apply a range of different focus offsets, without moving any optical component in the physical optical system, and without any loss of dynamic range.

The focus monitoring arrangement may be provided as part of a functional apparatus of which the same optical system is a part. Alternatively, the focus monitoring arrangement may be coupled to a functional apparatus and used for controlling operation of the other apparatus.

The invention further provides an inspection apparatus comprising an inspection illumination system for delivering inspection radiation to the target and an inspection detecting system for collecting the inspection radiation after being scattered by the target, wherein an optical system that forms part of one or both of the inspection illumination system and inspection detection system is provided with a focus monitoring arrangement according to the invention as set forth above.

These and further features and advantages of the invention will be apparent to the skilled reader from a consideration of the detailed description of examples that follows.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 3 depicts a known inspection apparatus arranged to perform angle-resolved scatterometry, as an example of an optical system in which a focus monitoring arrangement according to the present invention may be applied;

FIG. 4 illustrates the relationship between an illumination spot and a target grating in an example of the known scatterometers;

DETAILED DESCRIPTION OF EXEMPLARY EMBODIMENTS

Figure 1:
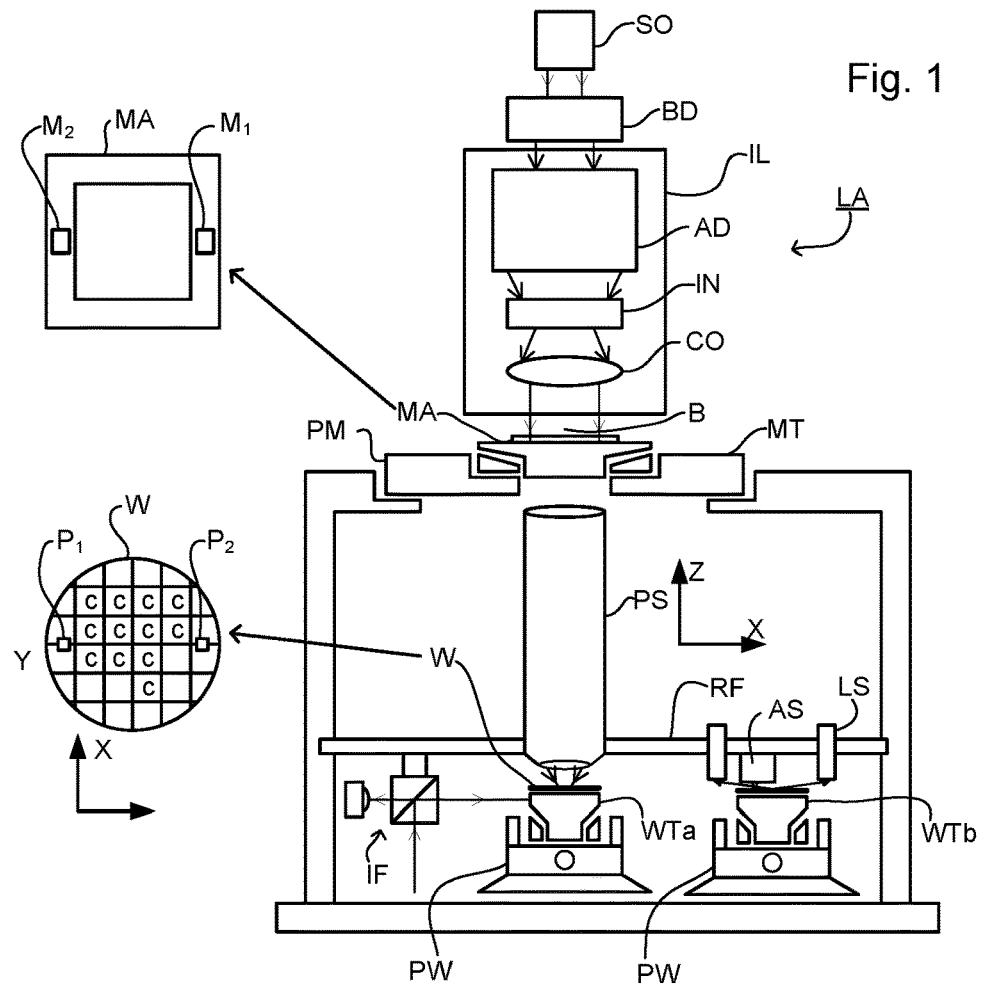
FIG. 1 depicts a lithographic apparatus.

FIG. 1 schematically depicts a lithographic apparatus. The apparatus comprises: an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
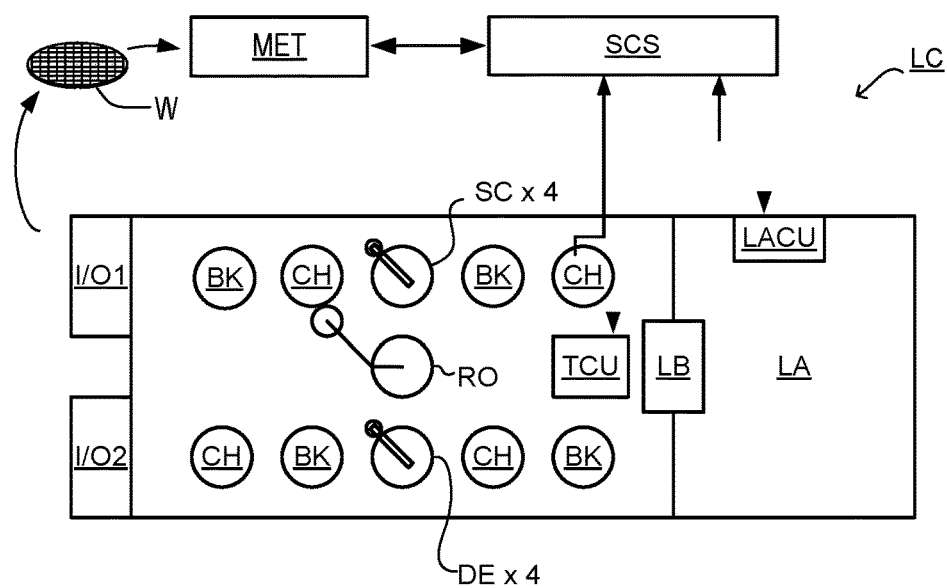
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a known scatterometer 300. In this device, the radiation emitted by radiation source 2 is collimated using lens system 12 and transmitted through interference filter 13 and polarizer 17, reflected by partially reflecting surface 16 and is focused into a spot S on substrate W via a microscope objective lens 15, which has a high numerical aperture (NA), preferably at least 0.9 and more preferably at least 0.95. Immersion scatterometers may even have lenses with numerical apertures over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate tables. Coarse and fine positioners may be provided to a second positioner PW configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle which one of those is moving in the real world, r if both are moving.

The reflected radiation then passes through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters. An aperture stop or spatial light modulator (not shown) may be provided in the illumination path to control the range of angle of incidence of radiation on the target.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processor PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of for instance FIG. 3 are described for example in published patent application US2006066855A1. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 3, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

FIG. 4 illustrates a plan view of a typical target 30, and the extent of illumination spot S in the scatterometer of FIG. 3. To obtain a diffraction spectrum that is free of interference from surrounding structures, the target 30 in the known method is a grating larger than the diameter of the illumination spot S. The diameter of spot S may be over 10 or 20 µm and the grating width and length may be 30 or 40 µm square. The grating in other words is 'underfilled' by the illumination, and the diffraction signal is free from interference by product features and the like outside the target grating itself. The illumination arrangement 2, 12, 13, 17 may be configured to provide illumination of a uniform intensity across a pupil plane of objective 15. Alternatively, but including an aperture in the illumination path, illumination may be restricted to on axis or off axis directions. As described in prior applications cited above, a modified scatterometer can use so-called dark field imaging to capture diffracted radiation from several smaller targets, all falling within the same illumination spot S.

Focus Monitoring with Electronic Focus Offset

Regardless of the type of inspection apparatus, or other optical system, it is general required to provide an automatic system for monitoring and adjusting focus of an optical system such as the system that forms the scatterometer in FIG. 3. If the spot S is not focused, then the illumination will fall on features other than the target 30, and the collected radiation will not allow an accurate measurement of the properties of the target. As mentioned already, focusing arrangements are known which pass a beam of radiation through the optical system and use some kind of detector system to obtain a signal representing focus error. For example, in published patent application US20080151228A, light reflected from the target is imaged onto two photodetectors with different focus offsets. Comparing the focused spot area between the two photodetectors allows an indication of defocus of the optical system to be obtained, and the direction of defocus to be identified. The US patent application illustrates various simple photodetectors that may be used to obtain a measure of spot area. The contents of that patent application are incorporated herein by reference. Other types of focus arrangement can be envisaged, and the present disclosure is not limited to the technique of US 20080151228 A.

A pending international patent application PCT/EP2015/070410, not published at the present priority date, discloses a modified focus monitoring arrangement and associated method in which lock-in detectors are used to monitor focus related properties of an exposure apparatus using a heterodyne interferometric technique. Such techniques can be used in combination with the focus offset control technique disclosed herein. the content of the international patent application are also incorporated by reference.

Figure 5:
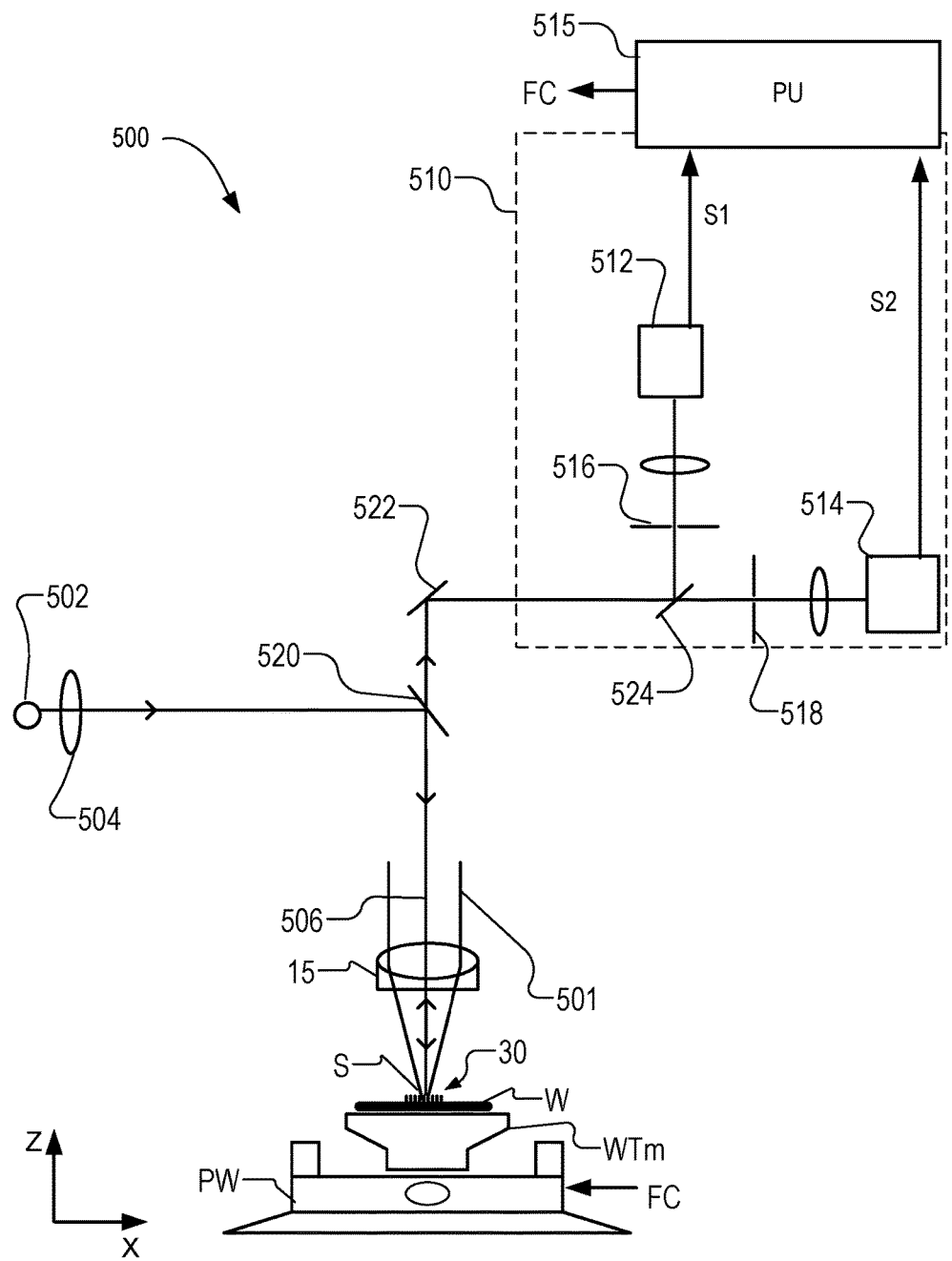
FIG. 5 is a schematic diagram of a known focus monitoring arrangement in an inspection apparatus.

FIG. 5 depicts in a simplified form a focus monitoring arrangement 500 of the type known from US 20080151228 A. FIG. 5 in particular provides a schematic view of optical paths for use in determining and controlling focus related properties of an inspection apparatus. With regard to the main function of the optical apparatus as a scatterometer or other inspection apparatus, a measurement illumination beam labeled 501 follows an illumination path comprising optical components 12, 13, 16, 17 (not shown in this drawing) and objective lens 15 (shown). A collection path comprising 15 for collecting radiation reflected by target 30 is also provided, as described above with reference to FIG. 3. The radiation collected by optical components of the collection path is directed to a detector 18 (not shown) connected to processor PU for target reconstruction or other purposes. The form and function of these may be the same as described above with reference to FIG. 3, and thus will not be discussed in this section. Target 30 may be formed on a substrate W that has been patterned and processed using the lithographic apparatus of FIG. 1 and the cluster of processing tools described above with reference to FIG. 2. The optical system including objective lens 15 is mentioned for the same of example only. It may be adapted for dark field imaging instead of or in addition to angle resolved scatterometry.

The focus monitoring arrangement and methods illustrated and described below can be applied in an optical system designed for a different kind of inspection (for example in a microscope), or for a purpose different from inspection (for example surface treatment, or optical recording). In particular, the arrangements of the present disclosure can also be applied to focusing of the projection system PS in the lithographic apparatus LA, or ancillary systems such as the alignment sensor AS. Indeed the optical system of the focus monitoring arrangement may or may not be part of (or share parts with) a functional optical system that is performing inspection or treatment of a target. The optical system of the focus monitoring arrangement may be ancillary to another functional system which is monitored and/or controlled indirectly using focusing of the optical system of the focus monitoring arrangement. In these cases, the optical system through which focusing is monitored is not the same as the functional system performing inspection and/or processing of the target. In the field of lithography, for example, the functional system may be an electron beam (e-beam) patterning apparatus, such as are used to make the reticle (patterning device) M. Other examples may be laser or mechanical machining or surface treatment apparatuses. Provided the focus monitoring arrangement is coupled to and calibrated with the functional system, a desired monitoring and/or control function may be implemented.

Focusing of the illumination spot S on target 30 is achieved by a suitable mechanism which may involve moving elements within the optical system, and/or moving the optical system and substrate bodily in relation to one another. For the sake of example in this illustration, substrate W is supported by a substrate table WTm similar to the substrate tables WTa and WTb of the lithographic apparatus. Positioners PW control the height of the substrate in response to a focus control signal FC generated by processor PU. Positioners PW control the position of substrate W in X and Y directions also, to bring each target of interest into position beneath the objective lens 15.

Focus monitoring arrangement 500 in this example comprises a radiation source 502 with an associated lens system 504. Focusing radiation 506 passes through objective lens 15 to be reflected from target 30. The arrangement further includes a focus detection system 510 including a first photodetector 512 a second photodetector 514. These components are arranged in an optical system which defines effectively several optical paths. Generally speaking, in the type of apparatus shown, there is an illumination system for illuminating the target with focusing radiation 506 and a collection system for collecting reflected radiation and delivering it to focus detection system 510. These individual systems together form a focus sensor.

The detectors 512, 514 may be single pixel photodiodes, or multi-pixels or multi-zone detectors, as described in the prior patent application mentioned above. Detection system 510 includes processor 515 that receives signals S1, S2 from photodetectors 512, 514 and uses these to generate focus control signal FC. Based on the technique of US 20080151228 A, each photodetector is arranged to measure, directly or indirectly, the cross-sectional area of the radiation beam in a plane slightly offset from a nominal back focal plane of objective lens 15. There are numerous ways to implement this. In a simple example, first photodetector 512 is positioned behind a first aperture 516 and second photodetector 514 is positioned behind a second aperture 518. The amount of light passing through each aperture will depend on how well the spot S is imaged on that aperture.

The operation of processor 515 using signals from the photodetectors to derive the focus control signal FC will be described further below. It may be envisaged that a processor 516 is implemented by software sharing the same processing hardware as processor PU shown in FIG. 3 for the metrology functions. However, a dedicated sub-processor can be provided to implement the focus monitoring and control functions, if desired.

The mentioned beam paths can be implemented in many different layouts, and a particular configuration of beam splitters 520, 522, 524 is shown schematically here, only for illustration of the principles of the design. Not shown in the drawing are numerous components that would be included in a practical system, including for example lenses or other focusing elements. These can be adapted readily from the known apparatus and do not need to be described in detail. Additional beam paths for different functions (for different types of measurement) can also be provided.

Figure 6A:
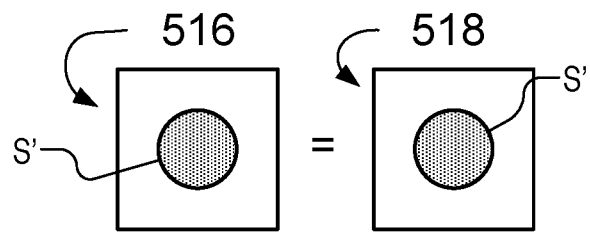
FIGS. 6A-6C illustrate a principle of focus determination in the focus monitoring arrangement of FIG. 5.
Figure 6B:
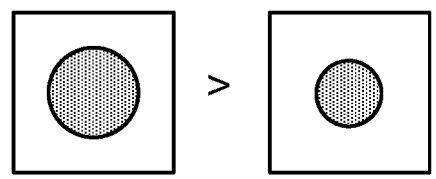
Figure 6C:
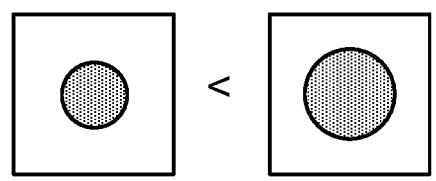

Referring briefly to FIG. 6, it may be recalled that a focus measurement can be derived by comparing the size of a radiation spot as seen by two photodetectors 512 and 514. The principles of this technique, as well as some variations that may be applied equally in the present arrangement, are described in the prior patent application US 20080151228 A, mentioned above. In this arrangement, the two apertures 516, 518 are arranged one in front and one behind a back focal plane of the optical system, also referred to as a field plane. That is to say, the two detectors are deliberately positioned to experience focus errors when the optical system is actually focused on the target. This deliberate defocus, as well as any actual focus error, influences the size of spot image S' on each aperture. When focus error is zero, spot images S' on both detectors will be equal (FIG. 6(a) situation). When focus error is non-zero in a first direction, spot image S' will spread over a greater area on aperture 512 and a smaller area on aperture 514 (FIG. 6(b) situation). This inequality of spatial extent (which may be measured in various ways) can be detected electronically. Similarly, when focus error is non-zero in an opposite direction, spot image S', the inequality will be reversed (FIG. 6(c) situation). These detected inequalities can be used to generate a focus error measurement, and hence to generate the focus control signal FC.

Figure 7:
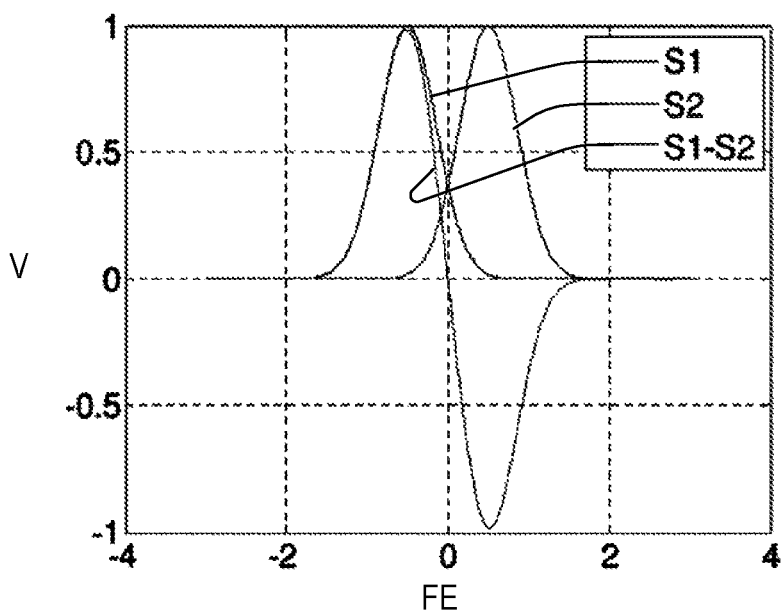
FIG. 7 illustrates the generation of a focus signal in the focus monitoring arrangement of FIG. 5.

FIG. 7 illustrates the form of signals S1 and S2 in an example of the apparatus of FIG. 5. On the horizontal axis, focus error FE is plotted on an arbitrary scale, which may be, for example, microns. On the vertical axis, a signal voltage is plotted, on an arbitrary scale. Each signal S1 and S2 shows a peak when they spot image S' is most tightly focused on the corresponding aperture 512 or 514. Because the planes of the apertures are offset, the peak in signal S1 is to the minus side of zero focus error say, FE=−0.5. The peak in signal S2 is slightly to the positive side of zero focus, say FE=0.5. Processor 515 calculates a difference signal S1-S2 which is also plotted on the graph. As can be seen, the difference signal exhibits a quasi-sinusoidal behavior, with a zero crossing at FE=0. In the vicinity of FE=0, the difference signal is roughly linear in form. The difference signal is therefore a focus error signal that can be used directly or indirectly to generate the focus control signal FC.

Now, in many applications, it may be designed to apply an offset in the focus control arrangement, and to vary the offset for different situations. In the example of the scatterometer of FIG. 3, it was mentioned that different wavelengths of inspection radiation may be used, and these wavelengths may differ from the wavelength of the focusing radiation 506. Consequently, due to chromatic aberration in the optical system of the scatterometer, a spot S of inspection radiation may be focused at a different height than a spot S of focusing radiation. Therefore, to achieve accurate focus of the inspection radiation, an offset should be applied when generating the focus control signal FC. There may be numerous other reasons why an offset is desired. For example, it may be designed to inspect layers beneath a top layer of the target, while the focus monitoring arrangement "sees" the top layer.

If the desired offset were constant, then it would be a simple matter to position the aperture is 516, 518 either side of an offset plane. However, there is in practice a desire for the offset to be controllable to different values rapidly, for example to permit rapid switching of wavelengths in the scatterometer of FIG. 3. Known methods for switching the offset have various drawbacks, as will now be illustrated.

Figure 8:
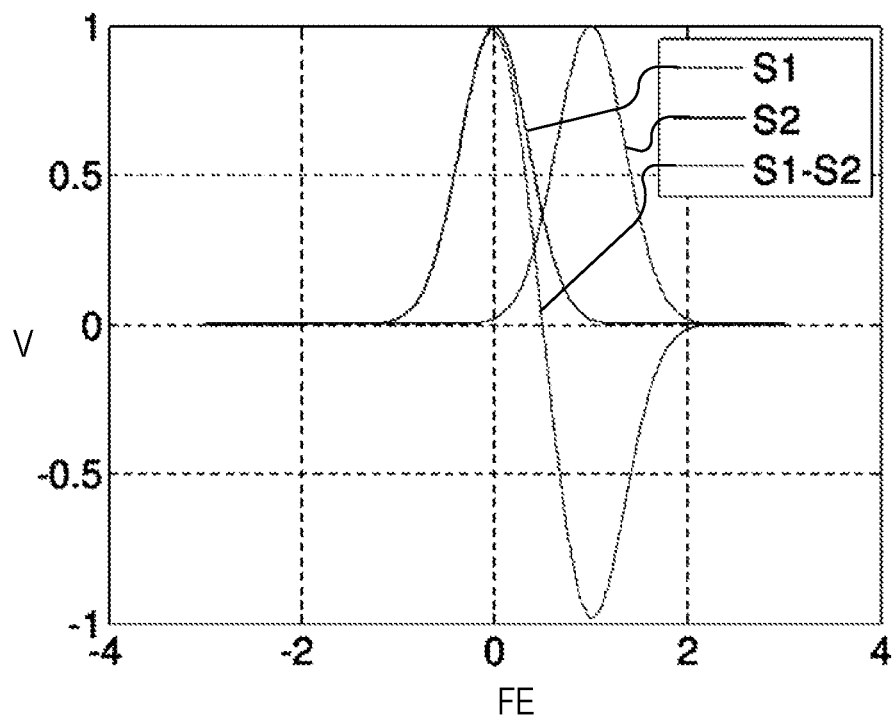
FIG. 8 illustrates the generation of a focus signal from two individual detector signals in an arrangement with a mechanical focus offset selector.

FIG. 8 illustrates signals S1, S2 and the difference signal S1-S2 in an example having an offset applied. On the focus error scale, the plane of first aperture 512 is positioned so that signal S1 has a peak at FE=0. The plane of second aperture 514 is positioned so that signal S2 has a peak at FE=1.0. The zero crossing of the difference signal is thus offset to a position FE=0.5. If the horizontal scale is measured in microns, the result is that the control apparatus will be focused to height 0.5 μm above the position where the spot S of focus radiation would actually be in focus. By providing some movable optical elements, the effective positions of the apertures 512, 514 can be shifted to achieve the offset shown in FIG. 8, without physically moving the apertures and photodetectors. Nevertheless, any mechanical switching limits the speed with which measurements with different offsets can be made.

Figure 9:
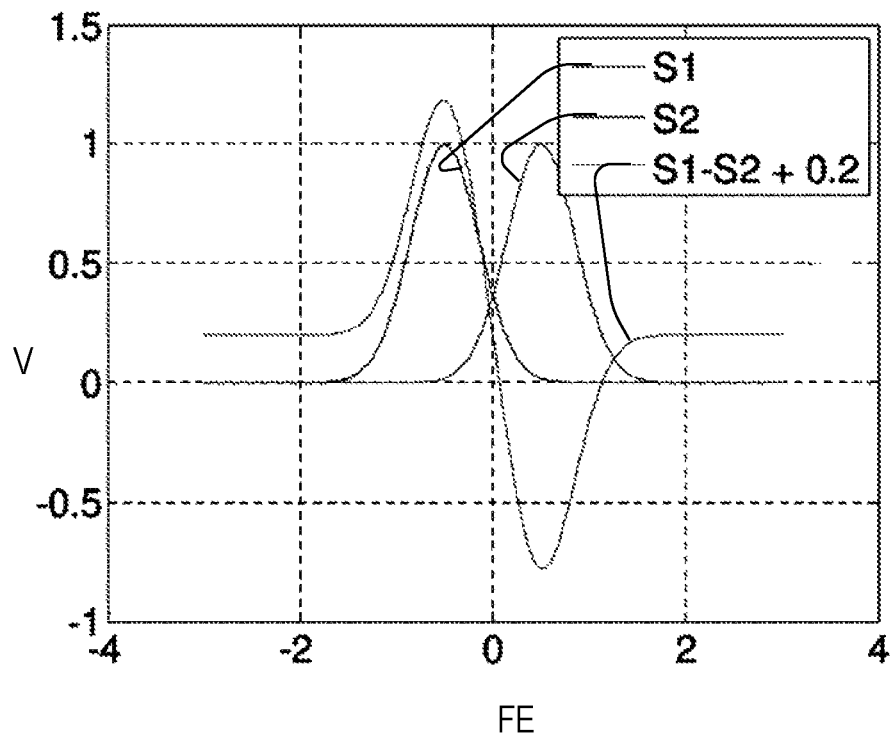
FIG. 9 illustrates the generation of a focus signal from two individual detector signals in a known arrangement having an electronic focus offset selector of known type.

FIG. 9 illustrates an alternative solution to providing a controllable offset. In this example, the difference signal S1-S2 is modified by the application of a variable numerical offset on the voltage scale. The example of an offset 0.2 is illustrated, which has the effect of shifting the zero crossing of the offset difference signal slightly higher than FE=0. Because this offset is applied electronically, or by calculation, it can be varied very quickly without mechanical disturbance. However, the relationship between voltage and height is quite uncertain, and therefore the amount of focus offset obtained for a given offset voltage is quite uncertain. Moreover, the difference signal provides only a finite linear region, and the usable dynamic range of the focus monitoring arrangement is reduced directly by the application of the offset voltage.

Figure 10:
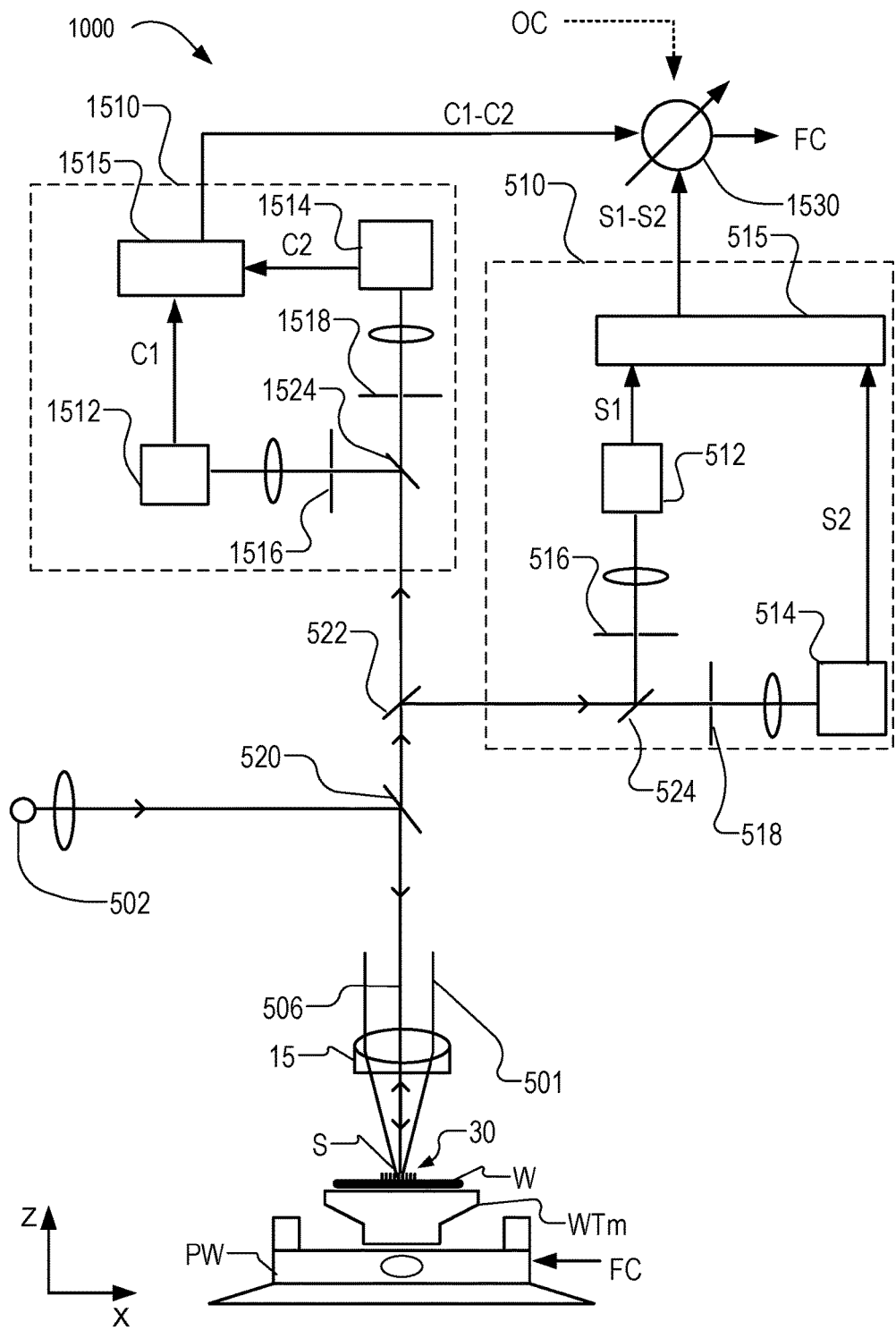
FIG. 10 is a schematic diagram of a focus monitoring arrangement having an electronic focus offset selector according to an embodiment of the present invention.

FIG. 10 illustrates a focus monitoring arrangement 1000 for generating a focus control signal FC with variable offset, avoiding the drawbacks mentioned above. Focus monitoring arrangement 1000 effectively forms two focus sensors, although they share an illumination system for illuminating the target with focusing radiation 506 and a collection system for collecting reflected radiation. The collected radiation is delivered to a first focus detection system 510, which can be the same as the one in FIG. 5, but also to a second focus detection system 1510. These individual systems together form a focus sensor. Second focus detection system 1510 comprises components 1512 to 1518 and 1524 similar to those in the first focus detection system 510. A photodetector 1512 produces a signal C1, whose peak depends on the position of an aperture 1516 relative to a back focal plane of the optical system including objective lens 15. A photodetector 1514 produces a signal C2, is peak depends on the position of an aperture 1518. As will be appreciated, the peaks and signals C1 and C2 can be positioned offset from the peaks in signals S1 and S2, by appropriate positioning of the four apertures 516, 518, 1516, 1518.

A first processor 515 produces a first difference signal S1-S2 which serves as a first focus error signal. The first focus error signal indicates focus error relative to a first reference distance, defined by the placing of the apertures 516, 518. The second processor 1515 produces a second difference signal C1-C2 which serves as a second focus error signal. The second focus error signal indicates focus error relative to a second reference distance, defined by the placing of the apertures 1516, 1518. The first and second focus error signals are combined by a processor 1530 to generate focus control signal FC. As with the processor 515 in the example of FIG. 5, processors 515, 1515, 1530 can be implemented as individual processors, or as software modules within a single programmed processor. The processors can be implemented by any desired combination of analog and/or digital circuitry, without changing the principles of the disclosed technique.

The third processor 1530 combines the first and second focus error signals in a proportion determined by an offset control parameter who see, which may be specified by an operator, by controller of the scatterometer or other working apparatus whose position is being controlled. By varying the proportions of the first and second focus error signals, a third focus error signal is obtained, which effectively measures focus relative to a third reference distance, which is not limited to either of the reference distances of the first and second focus detection systems 510, 1510. In this way, a variable offset can be implemented instantaneously by calculation, with no requirement for mechanical adjustment.

Figure 11:
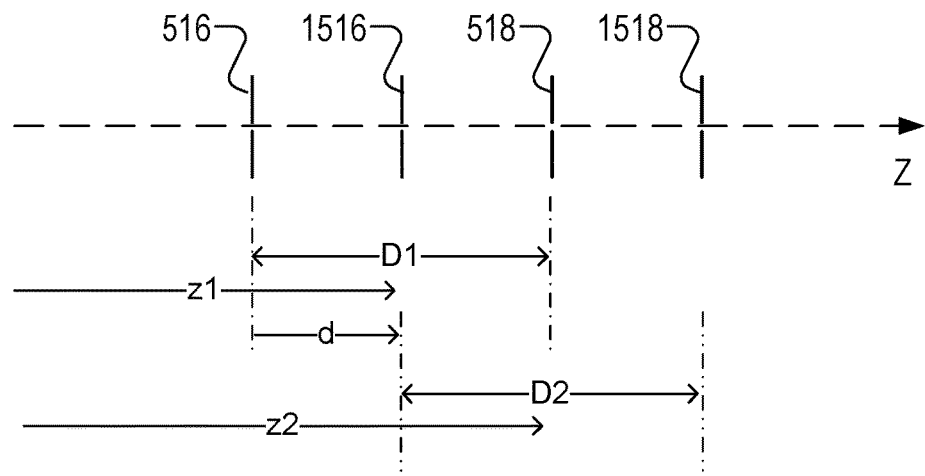
FIG. 11 illustrates schematically an arrangement of pinholes in an implementation of the focus monitoring arrangement of FIG. 10.
Figure 12:
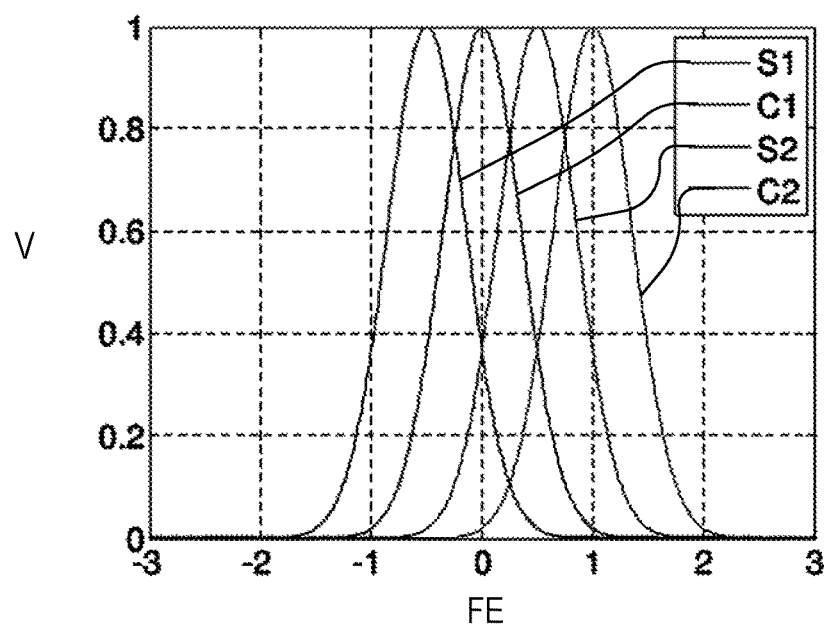
FIG. 12 illustrates four individual detector signals in the focus monitoring arrangement of FIGS. 10 and 11.

FIG. 11 illustrates schematically the placement of the apertures that are used to generate the first and second focus error signals, in one example of the focus monitoring arrangement of FIG. 10. This is only one convenient arrangement, and other arrangements are possible. FIG. 12 shows the peaks and the corresponding signals S1, S2, C1, C2 generated by the corresponding photodetectors. In this example, the apertures 516, 518 of the first focus detection system 510 are spaced apart by an amount D1. A midpoint between those apertures defines a first reference distance z1, which we shall define as FE=0 on the horizontal scale of the graph in FIG. 12. The apertures 1516, 1518 of the second focus detection system 1515 are spaced apart by an amount D2. A midpoint between those apertures defines a second reference distance z2 as marked.

In this example, the spacing D2 is equal to the spacing D1, and an offset d between the first and second reference distances is equal to half of that spacing. On the scale of the graph of FIG. 12, each spacing D1, D2 has the value of 1 μm, and the offset d has the value of 0.5 μm. Having the spacings equal to one another, and having offset of half the value of the spacing simplifies the calculations, as will be seen. In principle, however, any combination of spacings and offsets may be defined. Also, although first and second focus detection systems only illustrated in this example, there is nothing to prevent third, fourth, fifth etc. focus detection systems been provided, each with its own third, fourth, fifth reference distance. Apertures and photodetectors can be shared between these different focus detection systems, or they may be entirely separate. The third processor 1530 can combine any number of individual focus error signals in a desired proportion.

Figure 13:
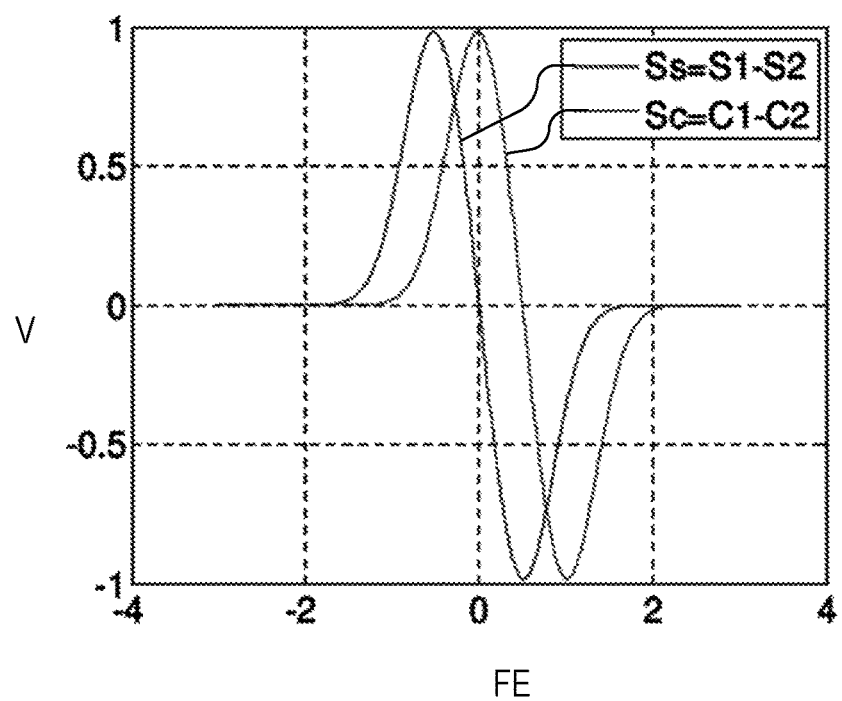
FIG. 13 illustrates the generation of first and second focus signals in the focus monitoring arrangement of FIGS. 10 and 11.

FIG. 13 illustrates the quasi-sinusoidal difference signals obtained by the two focus detection systems 510, 1510 in the example of FIG. 10. The first difference signal Ss=S1-S2 is identical to the one shown in FIG. 7, and indicates focus error relative to the first reference position corresponding to FE=0. The second difference signal Sc=C1-C2 has the same quasi-sinusoidal form, but indicates focus error relative to the second reference position corresponding to FE=d=0.5 in this example. Because of the selection of the spacings on the offsets, the second difference signal can be regarded as a quasi-cosine, when seen alongside the quasi-sine form of the first difference. By blending these signals in different proportions, a focus error signal can be obtained which has a zero crossing at any point in the range 0 to 0.5. In an example where more than two focus detection arrangements are provided, with different offsets, a wider range of zero crossing points can be defined.

Figure 14:
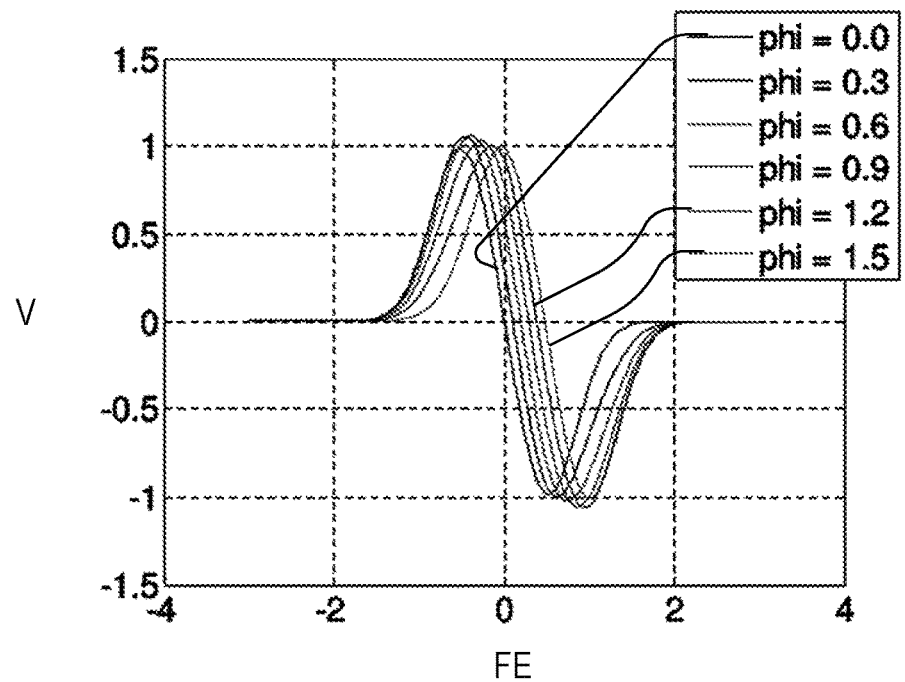
FIG. 14 illustrates the generation of different blended focus signals to implement electronic focus offset selection in the focus monitoring arrangement of FIGS. 10 and 11.

FIG. 14 illustrates the generation of a set of different focus error signals, with selectable offset values. In this example, the offset control parameter is defined as a phase value phi.

The blending of the first and second difference signals is defined by trigonometric functions of the phase value to generate a third focus error signal S(phi) using the equation:

$$S(phi)=\sin(phi)\cdot Ss+\cos(phi)\cdot Sc$$

According to this function, with the offset control parameter phi at zero, the focus control signal FC is determined entirely by the first focus error signal (first difference signal) Ss. Focus of the controlled apparatus will be determined by reference to reference distance z1 corresponding to FE=0 on the graph. As phi increases through different values towards 1.5 (i.e. π/2), a proportion of the second focus error signal Sc begins to increase and the proportion of the first focus error signal Ss decreases, so that the zero crossing of the calculated third focus error signal S(phi) corresponds to increasing values of FE. Thus, with the example values given, a focus monitoring arrangement with continuously variable offset values between zero and 0.5 μm has been realized.

Compared with known methods of adjusting focus offset, a change of calculation can be very fast. The linear range of the focus error signal is fully used and the dynamic range of the focus control servo loop is maintained. The shift is a function of the mechanical distance between the two detector pairs, so it is independent of the gain of the focus system. (This of course assumes that the gains of the first and second focus sensors are matched, which should be the case because they are effectively two shifted versions of the same arrangement.)

As mentioned before, an extension to multiple focus sensors, for example multiple detector pairs is feasible. Focus error signals can be generated from multiple pairs of photodetectors, for example, and physical photodetectors may be part of more than one pair.

The implementation of the first and second focus sensors need not be the same as illustrated here. Even within the principle of the arrangement of first and second focus detection systems having physically different reference distances, many different implementations are possible.

Moreover, the effect of having different reference distances can be obtained without the requirement for physically different reference distances. One way to do this, for example, would be to use to different wavelengths of focusing the radiation, and to use one of optical elements whose focusing power is markedly different at the different wavelengths. In order to obtain focus error signals corresponding to two reference distances, photodetectors 512, 514 etc. can be made to discriminate different colors. The different colors can be demultiplexed using dichroic filters as part of the beam splitters, or by using color filter is on the photodetectors, or at other points in between. Demultiplexing of different color signals can also be performed using the heterodyne interferometric technique described in the pending international patent application mentioned above.

Conclusion

By combining two or more focus signals, for example first and second focus error signals, in the manner described above, accuracy of focus control for different situations may be improved, without resorting to mechanical offset adjustment.

Although specific reference may be made in this disclosure to the use of focus monitoring and control arrangements in inspection apparatuses such as scatterometers, it should be understood that the disclosed arrangements may have application in other types of functional apparatuses, as mentioned already above.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A focus monitoring arrangement for an optical system, comprising:
   a first focus detection system comprising a first radiation detector and a second radiation detector, wherein the first focus detection system is configured to provide a first focus error signal indicating focus error relative to a first reference distance defined by placement of first and second apertures in the first focus detection system;
   a second focus detection system positioned a distance away from the first focus detection system and comprising a third radiation detector and a fourth radiation detector, wherein the second focus detection system is configured to provide a second focus error signal indicating focus error relative to a second reference distance defined by placement of third and fourth apertures in the second focus detection system, the second reference distance being offset from the first reference distance; and
   a processor configured to calculate a third focus error signal that indicates distance relative to a third reference distance, the third focus error signal being calculated by combining the first focus error signal and the second focus error signal.

2. The focus monitoring arrangement of claim 1, wherein the first focus error signal is a focus error signal having a zero crossing when a target is located at the first reference distance, and the second focus error signal is a focus error signal having a zero crossing when a target is located at the second reference distance.

3. The focus monitoring arrangement of claim 1, wherein the third focus error signal is a focus error signal having a zero crossing when a target is located at the third reference distance.

4. The focus monitoring arrangement of claim 1, wherein the processor is further configured to calculate the third focus error signal by a combination of the first focus error signal and the second focus error signal, each focus error signal being weighted in accordance with an offset parameter indicating the third reference distance.

5. The focus monitoring arrangement of claim 4, wherein the combination are weighted by trigonometric functions of the offset parameter.

6. The focus monitoring arrangement of claim 1, further comprising:
a focusing beam delivery system configured to deliver focusing radiation to the optical system, the optical system being arranged to deliver the focusing radiation to a target; and
a focusing beam collection system configured to collect the focusing radiation after reflection from the target;
wherein the first and second focus detection systems are configured to receive the collected focusing radiation and process the collected focusing radiation to generate the first and second focus error signals.

7. The focus monitoring arrangement of claim 6, wherein the first radiation detector is arranged to receive a first portion of the radiation and the second radiation detector is arranged to receive a second portion of the radiation, the first focus error signal being generated by comparing the first and second portions of radiation detected by the first and second radiation detectors.

8. The focus monitoring arrangement of claim 7, wherein one of the first and second radiation detectors is positioned in front of a conjugate of a reference plane front focal plane of the optical system and the other of the first and second radiation detectors is positioned behind a conjugate of a reference plane, the reference plane for the first focus detection system being different to the reference plane of the second focus detection system.

9. The focus monitoring arrangement of claim 6, wherein a common focusing beam delivery system and a common focusing beam collection system are shared by the first focus detection system and the second focus detection system.

10. The focus monitoring arrangement of claim 1, further comprising: a mechanism configured to adjust focus of the optical system on a target automatically in response to the calculated third focus error signal.

11. The focus monitoring arrangement of claim 10, wherein the mechanism configured to adjust focus is arranged simultaneously to adjust a functional system to which the optical system of the focus monitoring arrangement is coupled.

12. The focus monitoring arrangement of claim 1, further comprising: a controller for varying the third reference distance in accordance with varying operating parameters of the functional system.

13. An inspection apparatus comprising:
an inspection illumination system for delivering inspection radiation to the target; and
an inspection detecting system for collecting the inspection radiation after being scattered by the target,
wherein an optical system that forms part of one or both of the inspection illumination system and the inspection detection system is provided with a focus monitoring arrangement as claimed in claim 1.

14. The inspection apparatus of claim 13, wherein the optical system includes an objective lens, and wherein the same objective lens forms part of the inspection illumination system, the inspection detection system, the first focus detection system, and the second focus detection system.

15. The inspection apparatus of claim 13, wherein the third reference distance is varied to adjust performance of the focus monitoring arrangement as a wavelength of the inspection radiation is adjusted.

\* \* \* \* \*